United States Patent
Niazi et al.

(10) Patent No.: US 8,633,198 B1
(45) Date of Patent: Jan. 21, 2014

(54) SMALL MOLECULE INHIBITORS OF INFLUENZA A RNA-DEPENDENT RNA POLYMERASE

(71) Applicants: Kayvan Niazi, Encino, CA (US); Shahrooz Rabizadeh, Los Angeles, CA (US); Anne-Laure Le Ny, South Pasadena, CA (US); Oleksandr Buzko, Los Angeles, CA (US); Justin Golovato, Los Angeles, CA (US); Patrick Soon-Shiong, Los Angeles, CA (US)

(72) Inventors: Kayvan Niazi, Encino, CA (US); Shahrooz Rabizadeh, Los Angeles, CA (US); Anne-Laure Le Ny, South Pasadena, CA (US); Oleksandr Buzko, Los Angeles, CA (US); Justin Golovato, Los Angeles, CA (US); Patrick Soon-Shiong, Los Angeles, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 13/622,807

(22) Filed: Sep. 19, 2012

Related U.S. Application Data

(60) Provisional application No. 61/536,691, filed on Sep. 20, 2011.

(51) Int. Cl.
- *A01N 43/90* (2006.01)
- *A61K 31/519* (2006.01)
- *A01N 37/18* (2006.01)
- *A61K 38/00* (2006.01)
- *A61P 31/12* (2006.01)

(52) U.S. Cl.
USPC ........................................ 514/259.1; 514/3.7

(58) Field of Classification Search
None
See application file for complete search history.

(56) References Cited

FOREIGN PATENT DOCUMENTS

WO    WO 03095455 A2 *  11/2003

* cited by examiner

*Primary Examiner* — Jeffrey S. Lundgren
*Assistant Examiner* — Tori M Strong
(74) *Attorney, Agent, or Firm* — Fish and Associates, PC

(57) ABSTRACT

Antiviral compositions and methods are contemplated that are especially effective in the treatment and prevention of influenza A viruses. Also presented are cellular assays to identify small molecule compounds having antiviral properties, particularly as it relates to detection of influenza A RNA-dependent RNA polymerase activity in a mammalian cell independent of other influenza A components. Preferred assays allow for identification of viral replication inhibitors that do not disrupt normal cellular activity.

12 Claims, 6 Drawing Sheets

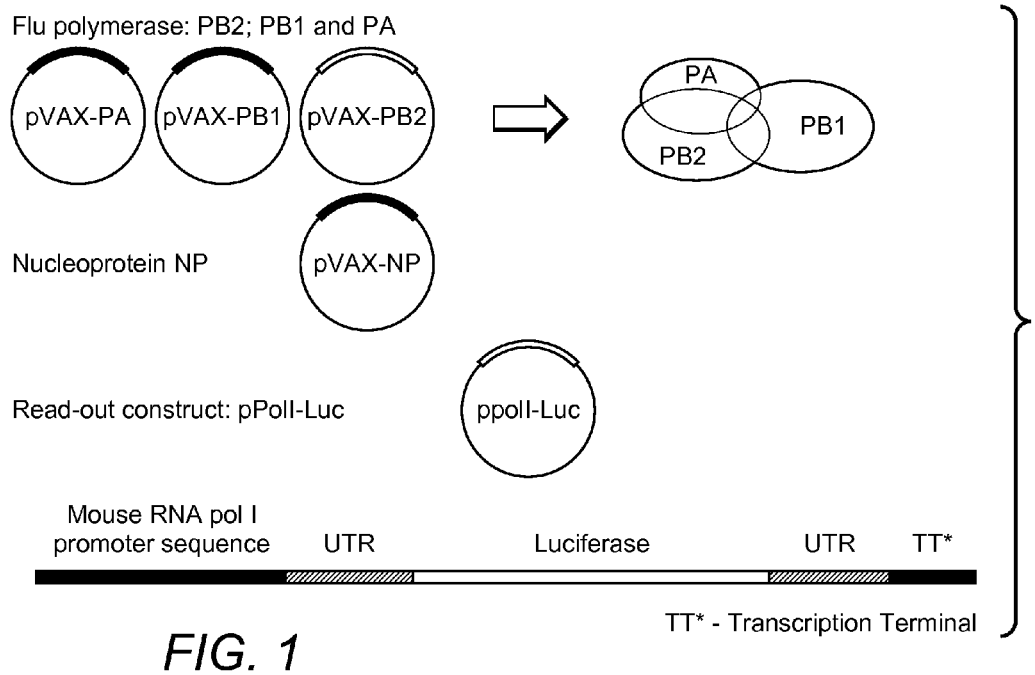
FIG. 1
FIG. 2
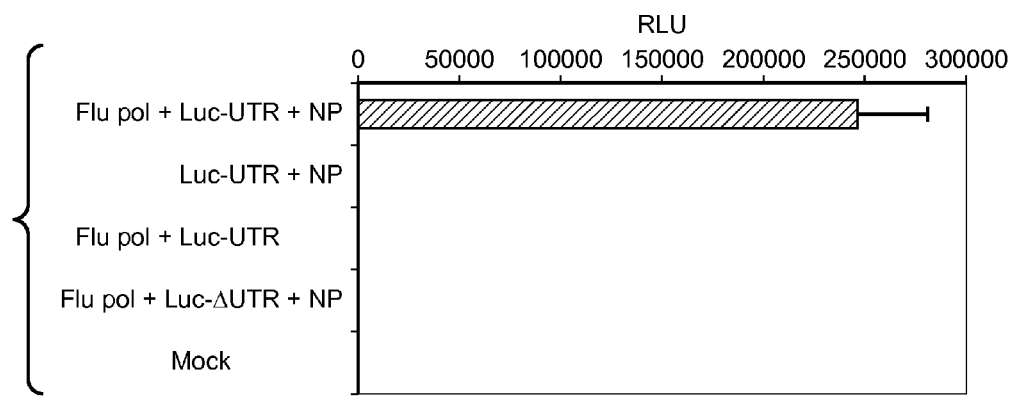

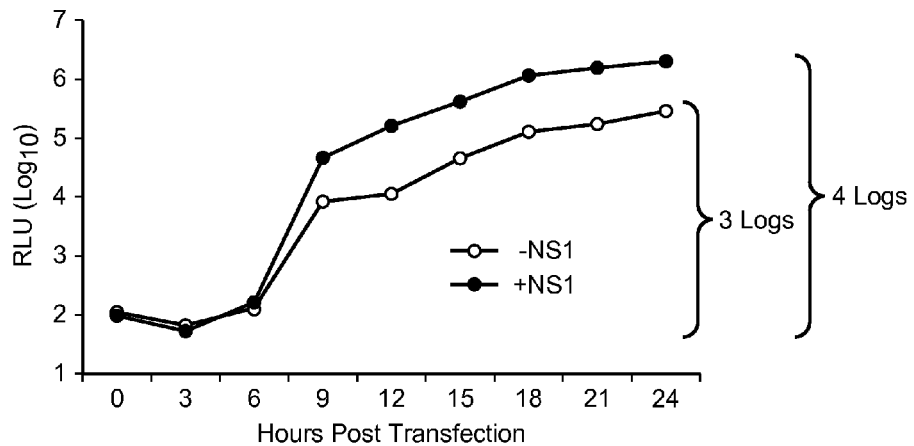
FIG. 3
FIG. 5
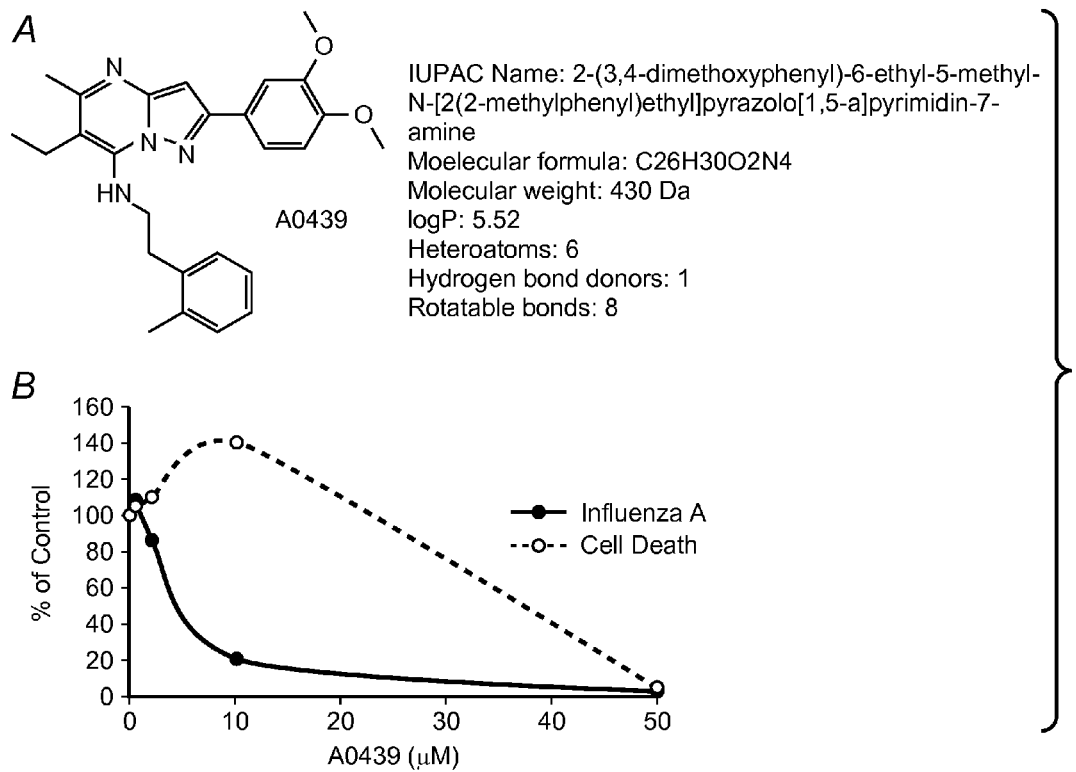

A0435

IUPAC Name: 2-(3,4-dimethoxyphenyl)-6-ethyl-5-methyl-N-[2(pyridin-2-yl)ethyl]pyrazolo[1,5-a]pyrimidin-7-amine
Moelecular formula: C24H27N5O2
Molecular weight: 417 Da
logP: 4.72
Heteroatoms: 7
Hydrogen bond donors: 1
Rotatable bonds: 8

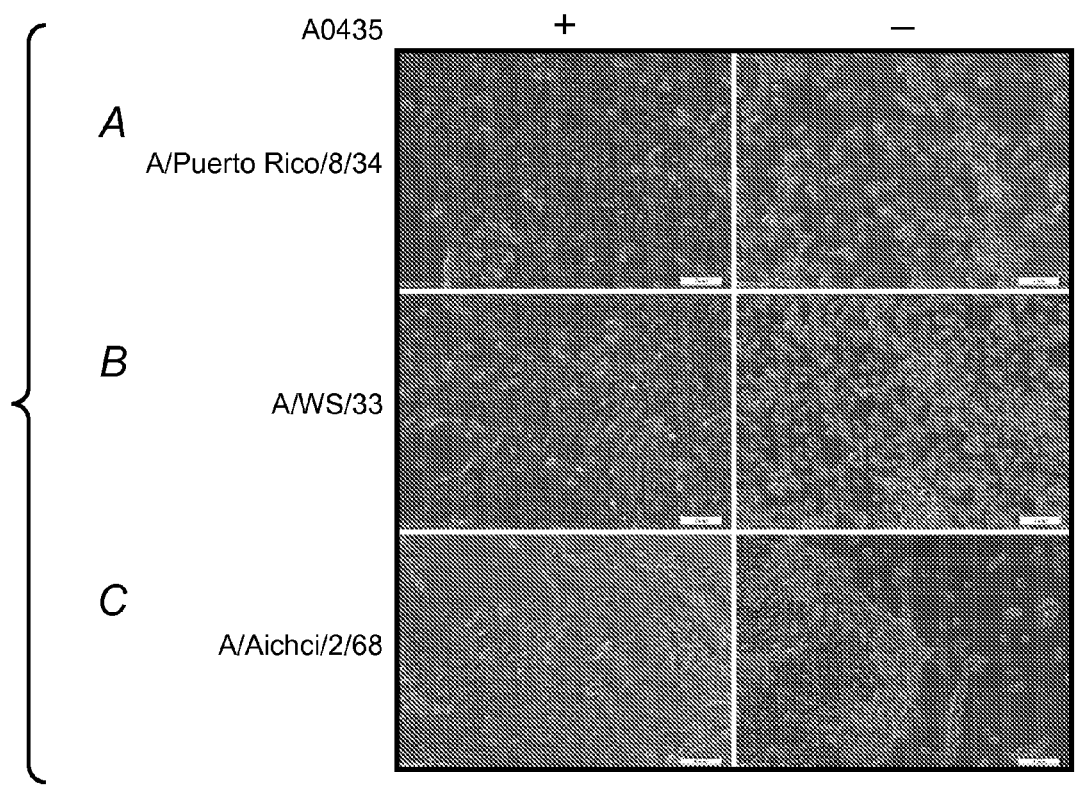
FIG. 8
FIG. 10
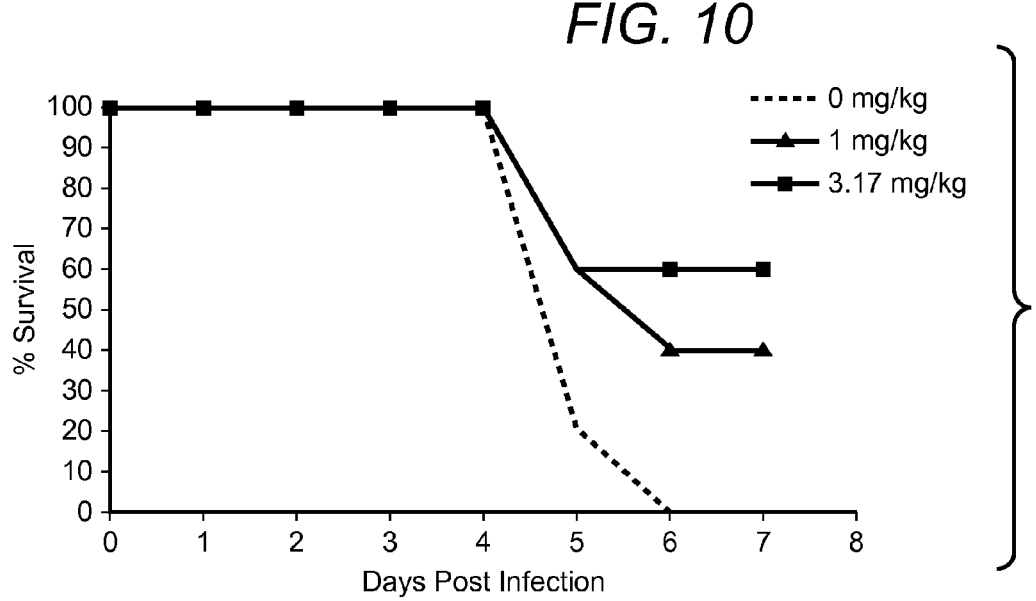

SMALL MOLECULE INHIBITORS OF INFLUENZA A RNA-DEPENDENT RNA POLYMERASE

This application claims priority to copending U.S. provisional application with the Ser. No. 61/536,691, which was filed Sep. 20, 2011.

FIELD OF THE INVENTION

The field of the invention is antiviral compounds and compositions.

BACKGROUND

Influenza A virus is a member of the orthomyxoviridae virus family of (−)-sense RNA viruses. The influenza A viral genome is composed of 8 segments or chromosomes which encode 11 proteins[1]. During infection, the virus-encoded RNA-dependent RNA polymerase (RdRP) converts the (−)-stranded RNAs to (+) strand messenger RNAs and a set of full length complementary genomic RNAs (or cRNAs) which serve as templates for genomic replication. Viral proteins expressed from the (+) strand messenger RNAs go about the task of establishing infection and facilitating viral replication, a process which ends in the amplification, assembly, and release of virus particles containing the initial 8 (−) strand chromosomes which repeat the infectious cycle.

The processes associated with the transcription and replication of the influenza A genome have been under investigation for decades. All eight chromosomes of every influenza A strain (including H1N1 seasonal, H1N1 "swine", H3N2, and H5N1 "avian") contain identical 5' and nearly identical 3' untranslated regions (UTRs) flanking the protein-coding portion of the sequence which otherwise encode distinct proteins. Experimental results demonstrate that the UTRs are recognized by RdRP as a promoter element and both components are critical for viral gene expression and replication. Hence, the viral polymerase and its cognate UTR RNA ligand are thought to control the viral life cycle and are critical targets for therapeutic intervention.

Despite such relatively detailed knowledge of viral replication, currently existing and clinically approved anti-influenza A therapeutic molecules are restricted to small molecules that inhibit one of two target classes of viral coat proteins: Neuraminidase (NA) and Matrix 2 (M2). NA belongs to a broad class of glycoside hydrolase enzymes (also known as sialidases, as N- or O-linked neuraminic acids are collectively called sialic acid) which cleave terminal sialic acid residues off virions and host cell receptor proteins. During influenza A infection, NA activity is involved in viral transit through mucus secretions of the respiratory tract as well as for the biochemical separation/elution of secreted viruses from the infected cells serving as sites of replication, thereby enabling the infection of nearby healthy cells. Currently, oseltamivir (trade name Tamiflu®) and zanamivir (trade name Relenza®) are two clinically approved medications for the treatment of influenza infection through inhibition of NA while laninamivir (Inavir) and peramivir are currently in the late stages of clinical trials as next-generation influenza NA inhibitors.

Unlike NA, influenza M2 is produced by the alternative splicing of the mRNA encoding the viral structural protein, matrix (or M). In contrast to M which is one of the most highly abundant viral proteins in infection and serves as a scaffold to which viral coat proteins and ribonucleoprotein particles bind, M2 is present in minute amounts in virions and serves as an ion channel which enables viral uncoating and escape from endosomal compartments into the cellular cytoplasm, a critical step in replication. Clinically approved inhibitors of M2 include amantadine (trade name Symmetrel®) and rimantadine (trade name Flumadine®).

NA and M2 inhibitors serve as successful proof-of-concept small molecule inhibitors of critical steps in the influenza virus infection cycle. Despite their early successes, however, use of both NA and M2 inhibitors has met recent challenges in treating influenza infection through the emergence of viral variants exhibiting drug resistance. For example, evidence of viral resistance to Tamiflu has been documented in numerous clinically relevant influenza A isolates including the 2009 pandemic[5], H3N2[6], H5N1[7], and seasonal H1N1[8] where resistance existed in 99.6% of circulating isolates in 2008. Although influenza A resistance to zanamivir has yet to be reported, the report of an influenza B viral isolate resistant to this agent[9] may indicate the possibility of future more prevalent resistance to this drug upon broad usage to treat influenza infections although the resistant virus described in this study had acquired an additional compensatory mutation in the HA protein which should reduce this possibility significantly. With regards to the M2 inhibitors, the Centers for Disease Control and Prevention indicated that nearly all circulating H3N2 and pandemic H1N1 virus isolates during the fall of 2009 were resistant to amantadines[10].

Unfortunately, surveillance efforts have also identified the recent emergence of dual oseltamivir/adamantane resistant isolates[11] indicating the need for the discovery and utilization of additional small molecule inhibitors targeting other critical viral targets. Thus, there is still a need to provide new and/or improved antiviral drugs that interfere with viral replication, and especially RNA-virus replication.

SUMMARY OF THE INVENTION

The inventors have discovered various compositions and methods that interfere with the infectious life cycle of influenza A, and most likely with viral replication. Moreover, the inventors have also discovered components and methods for a cellular assay to identify small molecule compounds having antiviral properties. In especially preferred aspects, the assay allows for detection of influenza A RNA-dependent RNA polymerase activity in a mammalian cell independent of other influenza A components, and allows for identification of inhibitors of viral replication that do not disrupt normal cellular activity.

In another aspect of the inventive subject matter, selected compounds are provided with antiviral properties. Particularly preferred compounds (A0435) were evaluated in an in vitro viral propagation system utilizing three different influenza A strains representing two different serotypes of virus and found to inhibit all three viruses at low μM concentrations and to prevent host cells from displaying virus-induced cytopathic effects (CPE). Consistent with these results, certain compounds, and especially A0435, also demonstrated antiviral activity in a live infection mammalian model of influenza A.

Various objects, features, aspects and advantages of the present invention will become more apparent from the following detailed description of preferred embodiments of the invention.

BRIEF DESCRIPTION OF THE DRAWING

FIG. 1 is a schematic of an Influenza A reporter assay construct.

FIG. 2 is a graph indicating requirements of components in a luciferase assay.

FIG. 3 is a graph depicting exemplary results for enhancement of expression in a luciferase assay.

FIG. 5A depicts the structure of another exemplary compound, and FIG. 5B is a graph illustrating dose response of the reporter system to the exemplary compound of FIG. 5A.

FIG. 8A-8C are photographs illustrating inhibition of cytopathic effects in selected cells by an exemplary compound.

FIG. 10 is a graph illustrating increase in survival following live infection using an exemplary compound.

DETAILED DESCRIPTION

Figure 4:
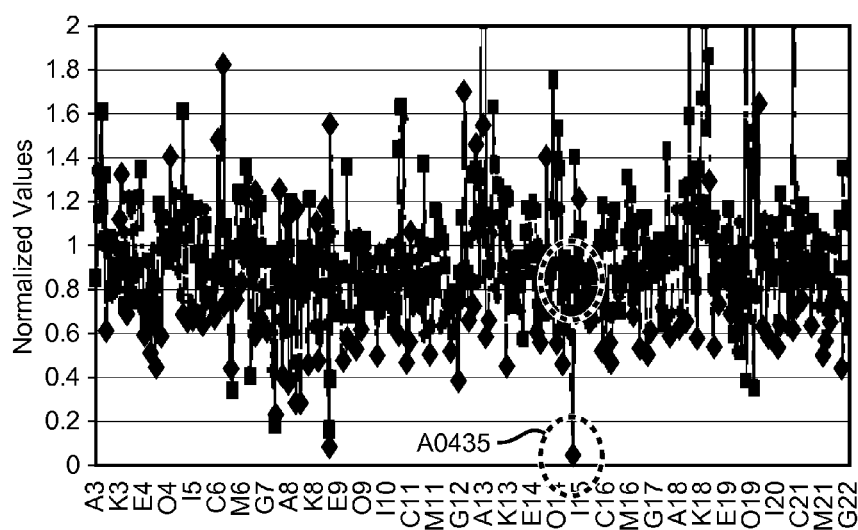
FIG. 4A is a schematic of raw data from a high-throughput screen demonstrating specific inhibition of the reporter system by an exemplary compound.
FIG. 4B depicts the structure of the exemplary compound.
FIG. 4C is a graph illustrating dose response of the reporter system to the exemplary compound.
Figure 4:
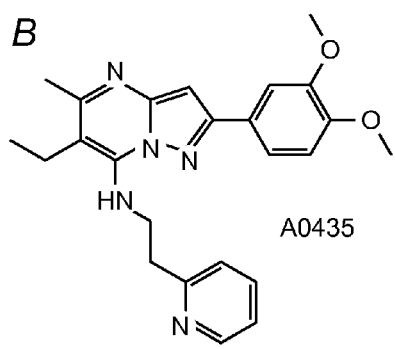
Figure 4:
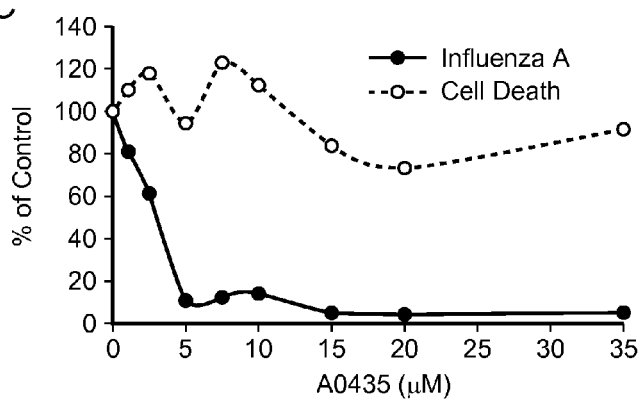

Based on a newly developed ultra-sensitive cell based assay utilizing an RdRP-based reporter system, several compounds were discovered (e.g., A0435 and A0439) with significant anti-viral activity against an apparently conserved viral target (most likely the viral replication and/or gene expression machinery).

To enable high-throughput identification of novel small molecule inhibitors of RdRP activity using a cell-based assay system, the inventors generated a panel of constructs encoding the influenza RdRP subunit proteins (PB2, PB1, and PA and the accessory NP protein) and a reporter RNA for expression in mammalian cells, and a typical assay system is schematically described in FIG. 1. The construct encoding the reporter RNA was designed to utilize a mouse RNA polymerase I promoter expression cassette to drive the transcription of an anti-sense RNA encoding firefly luciferase flanked by appropriate viral RNA domains. Transfection of these constructs into mouse B16-F10 cells demonstrates a robust signal in cells transfected with all five plasmids (e.g., encoding PA, PB1, PB2, NP, and the RNA polymerase I-driven luciferase RNA construct), but no detectable expression when any of these constituents were removed or in the presence of reporter RNA devoid of UTR-based promoter elements as illustrated in FIG. 2. A similar approach using a human expression cassette and a different viral serotype has been previously reported[2].

In a particularly preferred modification, a sixth construct was simultaneously included driving the expression of the viral non-structural 1 (NS1) protein. NS1 and NS2 are alternate mRNA splice isoforms encoded by segment 8 of the influenza A virus. NS1 performs a wide variety of functions during viral infection including regulation of viral RNA synthesis and enhancing viral protein translation[3] while NS2 is critical for viral RNA export from the host cell nucleus[4]. The inventors found that expression of NS1 resulted in an amplification of signal strength by approximately tenfold without altering the background "noise" of the system (FIG. 3) in a kinetic study. The inventors also found that the preferred window of time for the addition of potential inhibitors resides within the first 6 hours following removal of transfection DNA/liposome complexes (or "lipoplexes") prior to the appearance of detectable reporter activity. Exemplary data illustrating the increase in sensitivity.

Of course, it should be appreciated that the inventive subject matter need not be limited to the specific components as shown in the Figures and description below, but may include one or more modified nucleic acids. For example, the RdRP subunit proteins may be from a different virus, and/or may be mutated to reflect drug resistant mutant strains or to confer various further advantages. Similarly, the reported gene need not be limited to luciferase, but may be any other reported gene or system. Thus, the signal may be generated as an optical signal (luminescence, fluorescence, quenching, etc.), as a chemically identifiable signal (e.g., via protease action or antigen production), and/or as a biological signal (e.g., cell death, or phenotypic change). Similarly, the nucleic acids may be at least partially integrated into a single nucleic acid for transfection, or cells may be transiently or permanently transfected (as a cell line or transgene) to express the RdRP subunit proteins.

Regardless of the particular configuration, it should be appreciated that using such assay system as a biological screen, large and diverse chemical libraries can be readily interrogated. As a simultaneous counter screen, the inventors evaluated the same screened samples in a separate reporter system utilizing a cell death-activated reporter construct to distinguish between compounds that specifically inhibit viral RdRP and those that non-specifically inhibit mammalian gene transcription and/or alternatively activate a common cell death pathway in human cells where either result could be indicative of undesirable downstream toxicity.

Using these assays and search criteria, the inventors identified, inter alia, small molecule A0435 (see FIG. 4*a,b*). Dose titration studies of A0435 on the assay system demonstrated a 50% inhibitory concentration (IC50) of approximately 3 μM and there was no visible inhibitory impact on the level of constitutive gene expression provided by the counter-screen assay (see FIG. 4*c*). A second, structurally similar compound, A0439, was also tested in the reporter assay and found to show similar inhibition of the reporter system, albeit with an IC50 approximating 5 μM (see FIG. 5*a,b*) and increased toxicity at higher doses due to precipitation.

Of course, it should be appreciated that numerous other compounds having a scaffold that includes a pyrazolopyrimidine (or similar structure as shown in Table 1 below) are also deemed suitable, wherein such scaffolds will include various substituents as illustrated below. Most preferably, and with particular respect to compounds A0435 and A439, it is contemplated that the pyrazolopyrimidine core (or alternative scaffold) will include an alkoxyaryl or dialkoxyaryl moiety, which may be further optionally substituted. In such compounds, at least one oxygen atom may also be replaced with a primary, secondary, or tertiary amine, or with a sulfur or selenium atom. Most typically, the aryl is a phenyl or a heteroaryl (preferably with a nitrogen heteroatom). Likewise, the ethylpyridine moiety may be replaced by any alkylheteroaryl or alkylaryl, and one or both of the alkyl moieties at the pyrazolopyrimidine core may be replaced by a substituted alkyl, a heteroaryl, or that the two alkyl groups may form a ring. Remarkably, however, several positions at the scaffold could not be modified without concomitant loss or significant reduction in inhibitory action and/or increase in toxicity as is readily evident from the compounds listed in Table 1.

| Comp. | Structure | IUPAC Name | IC50 |
|---|---|---|---|
| A0436 | 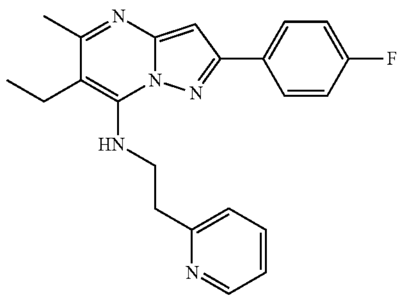 [SMILES: CCc1c(C)nc2cc(-c3ccc(F)cc3)nn2c1NCCc1ccccn1] | 6-ethyl-2-(4-fluorophenyl)-5-methyl-N-(2-(pyridin-2-yl)ethyl)pyrazolo[1,5-a]pyrimidin-7-amine | >10 uM (toxic to both antiviral and counterscreen at 50 uM) |
| A0437 | 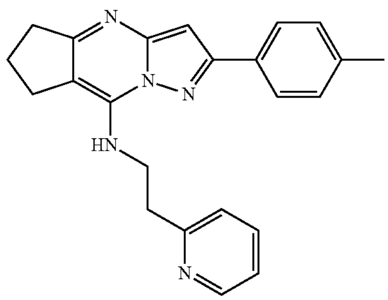 [SMILES: Cc1ccc(-c2cc3nc4c(c(NCCc5ccccn5)n3n2)CCC4)cc1] | N-(2-(pyridin-2-yl)ethyl)-2-p-tolyl-6,7-dihydro-5H-cyclopenta[d]pyrazolo[1,5-a]pyrimidin-8-amine | >50 uM (no observed toxicity or efficacy in either assay tested) |
| A0438 | 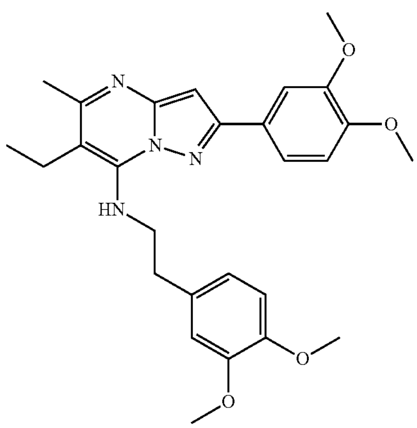 [SMILES: CCc1c(C)nc2cc(-c3ccc(OC)c(OC)c3)nn2c1NCCc1ccc(OC)c(OC)c1] | N-(3,4-dimethoxyphenethyl)-2-(3,4-dimethoxyphenyl)-6-ethyl-5-methylpyrazolo[1,5-a]pyrimidin-7-amine | >10 uM (toxic to both antiviral and counterscreen at 50 uM) |
| A0440 | 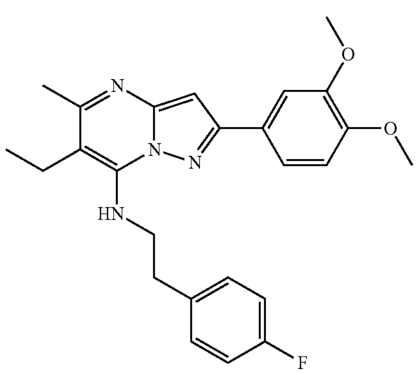 [SMILES: CCc1c(C)nc2cc(-c3ccc(OC)c(OC)c3)nn2c1NCCc1ccc(F)cc1] | 2-(3,4-dimethoxyphenyl)-6-ethyl-N-(4-fluorophenethyl)-5-methylpyrazolo[1,5-a]pyrimidin-7-amine | >50 uM (no observed toxicity or efficacy in either assay tested) |

| Comp. | Structure | IUPAC Name | IC50 |
|---|---|---|---|
| A0441 | 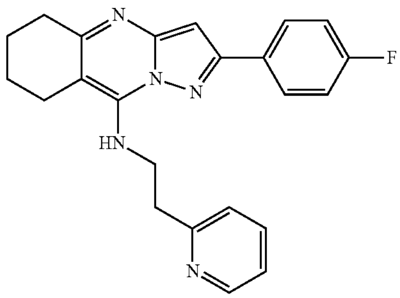 [SMILES: Fc1ccc(-c2cc3nc4c(c(NCCc5ccccn5)n3n2)CCCC4)cc1] | 2-(4-fluorophenyl)-N-(2-(pyridin-2-yl)ethyl)-5,6,7,8-tetrahydropyrazolo[5,1-b]quinazolin-9-amine | >10 uM (toxic to both antiviral and counterscreen at 50 uM) |
| A0442 | 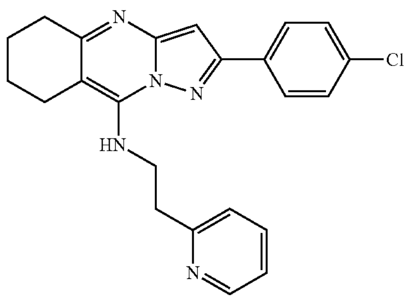 [SMILES: Clc1ccc(-c2cc3nc4c(c(NCCc5ccccn5)n3n2)CCCC4)cc1] | 2-(4-chlorophenyl)-N-(2-(pyridin-2-yl)ethyl)-5,6,7,8-tetrahydropyrazolo[5,1-b]quinazolin-9-amine | >10 uM (toxic to both antiviral and counterscreen at 50 uM) |
| A0443 | 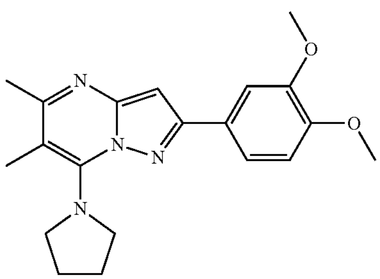 | 2-(3,4-dimethoxyphenyl)-5,6-dimethyl-7-(pyrrolidin-1-yl)pyrazolo[1,5-a]pyrimidine | >50 uM (no observed toxicity or efficacy in either assay tested) |
| A0444 | 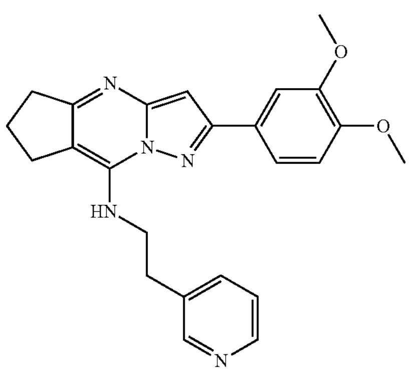 [SMILES: COc1ccc(-c2cc3nc4c(c(NCCc5cccnc5)n3n2)CCC4)cc1OC] | 2-(3,4-dimethoxyphenyl)-N-(2-(pyridin-3-yl)ethyl)-6,7-dihydro-5H-cyclopenta[d]pyrazolo[1,5-a]pyrimidin-8-amine | >10 uM (toxic to both antiviral and counterscreen at 50 uM) |
| A0445 | 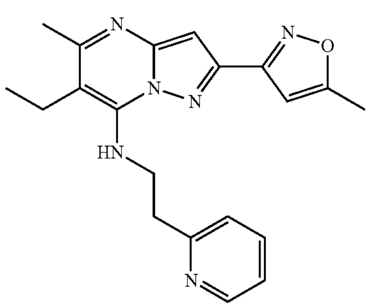 [SMILES: CCc1c(C)nc2cc(-c3cc(C)on3)nn2c1NCCc1ccccn1] | 6-ethyl-5-methyl-2-(5-methylisoxazol-3-yl)-N-(2-(pyridin-2-yl)ethyl)pyrazolo[1,5-a]pyrimidin-7-amine | >50 uM (no observed toxicity or efficacy in either assay tested) |

-continued

| Comp. | Structure | IUPAC Name | IC50 |
|---|---|---|---|
| A0525 | 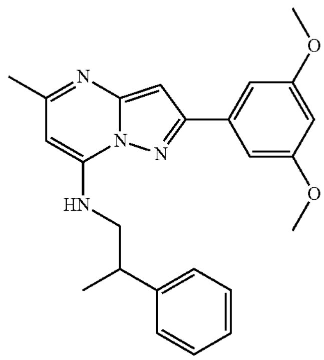 [SMILES: COc1cc(OC)cc(-c2cc3nc(C)cc(NCC(C)c4ccccc4)n3n2)c1] | 2-(3,5-dimethoxyphenyl)-5-methyl-N-(2-phenylpropyl)pyrazolo[1,5-a]pyrimidin-7-amine | >50 uM (no observed toxicity or efficacy in either assay tested) |
| A0526 | 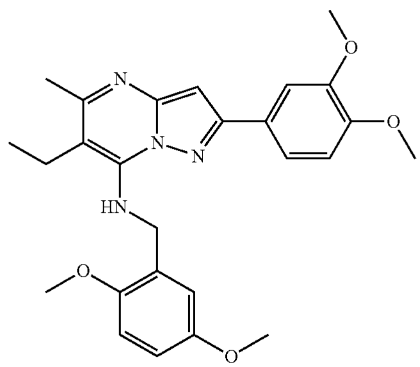 [SMILES: CCc1c(C)nc2cc(-c3ccc(OC)c(OC)c3)nn2c1NCc1cc(OC)ccc1OC] | N-(2,5-dimethoxybenzyl)-2-(3,4-dimethoxyphenyl)-6-ethyl-5-methylpyrazolo[1,5-a]pyrimidin-7-amine | >50 uM (no observed toxicity or efficacy in either assay tested) |
| A0527 | 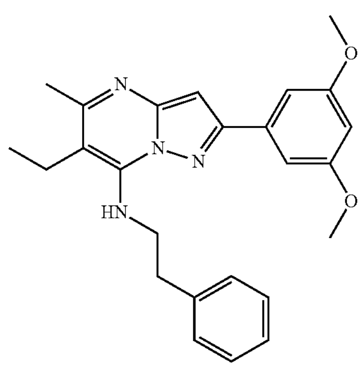 [SMILES: CCc1c(C)nc2cc(-c3cc(OC)cc(OC)c3)nn2c1NCCc1ccccc1] | 2-(3,5-dimethoxyphenyl)-6-ethyl-5-methyl-N-phenethylpyrazolo[1,5-a]pyrimidin-7-amine | >50 uM (no observed toxicity or efficacy in either assay tested) |
| A0528 | 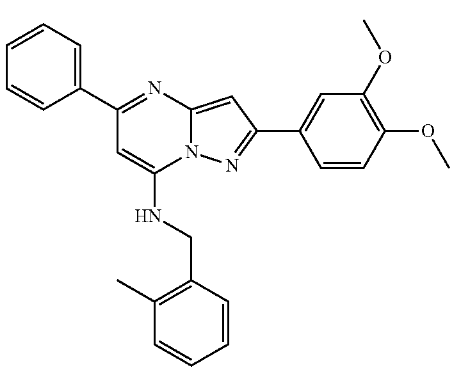 [SMILES: COc1ccc(-c2cc3nc(-c4ccccc4)cc(NCc4ccccc4C)n3n2)cc1OC] | 2-(3,4-dimethoxyphenyl)-N-(2-methylbenzyl)-5-phenylpyrazolo[1,5-a]pyrimidin-7-amine | >50 uM (no observed toxicity or efficacy in either assay tested) |

-continued

| Comp. | Structure | IUPAC Name | IC50 |
|---|---|---|---|
| A0529 | 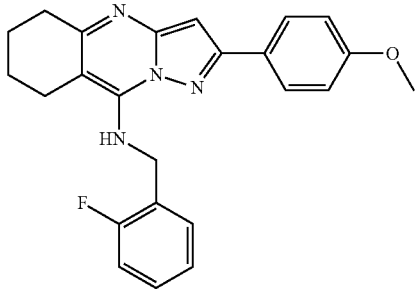 [SMILES: COc1ccc(-c2cc3nc4c(c(NCc5ccccc5F)n3n2)CCCC4)cc1] | N-(2-fluorobenzyl)-2-(4-methoxyphenyl)-5,6,7,8-tetrahydropyrazolo[5,1-b]quinazolin-9-amine | >50 uM (no observed toxicity or efficacy in either assay tested) |
| A0530 | 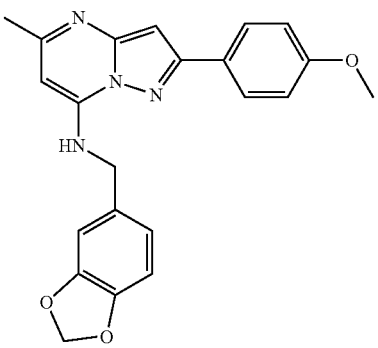 | N-(benzo[d][1,3]dioxol-5-ylmethyl)-2-(4-methoxyphenyl)-5-methylpyrazolo[1,5-a]pyrimidin-7-amine | >50 uM (no observed toxicity or efficacy in either assay tested) |
| A0531 | 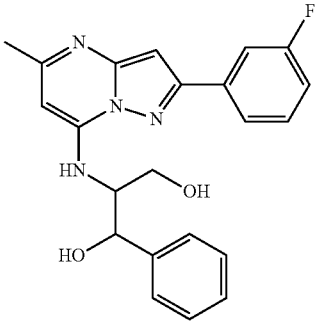 [SMILES: Cc1cc(NC(CO)C(O)c2ccccc2)n2nc(-c3cccc(F)c3)cc2n1] | 2-(2-(3-fluorophenyl)-5-methylpyrazolo[1,5-a]pyrimidin-7-ylamino)-1-phenylpropane-1,3-diol | >50 uM (no observed toxicity or efficacy in either assay tested) |
| A0532 | 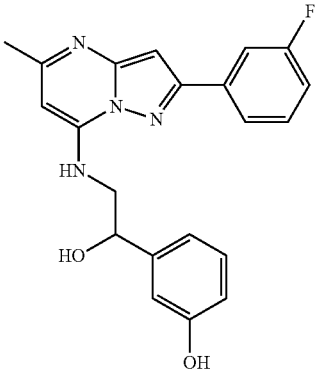 [SMILES: Cc1cc(NCC(O)c2cccc(O)c2)n2nc(-c3cccc(F)c3)cc2n1] | 3-(2-(2-(3-fluorophenyl)-5-methylpyrazolo[1,5-a]pyrimidin-7-ylamino)-1-hydroxyethyl)phenol | >50 uM (no observed toxicity or efficacy in either assay tested) |

-continued

| Comp. | Structure | IUPAC Name | IC50 |
|---|---|---|---|
| A0547 | 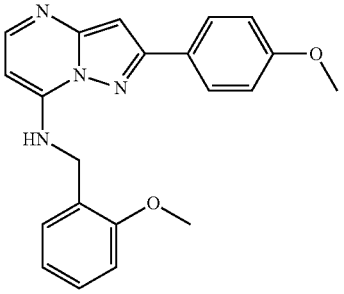 [SMILES: COc1ccc(-c2cc3nccc(NCc4ccccc4OC)n3n2)cc1] | N-(2-methoxybenzyl)-2-(4-methoxyphenyl)pyrazolo[1,5-a]pyrimidin-7-amine | >50 uM (no observed toxicity or efficacy in either assay tested) |
| A0548 | 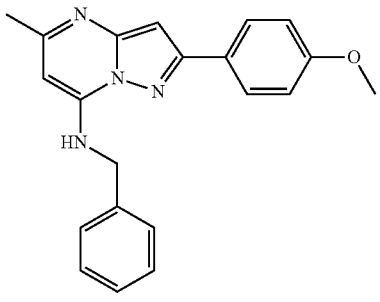 | N-benzyl-2-(4-methoxyphenyl)-5-methylpyrazolo[1,5-a]pyrimidin-7-amine | >50 uM (no observed toxicity or efficacy in either assay tested) |
| A0549 | 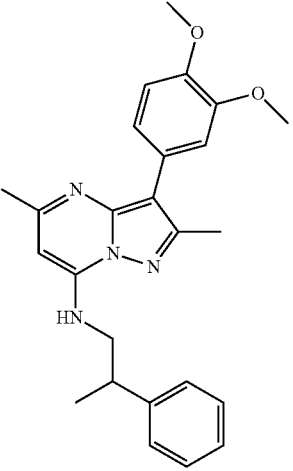 | 3-(3,4-dimethoxyphenyl)-2,5-dimethyl-N-(2-phenylpropyl)pyrazolo[1,5-a]pyrimidin-7-amine | >50 uM (no observed toxicity or efficacy in either assay tested) |
| A0550 | 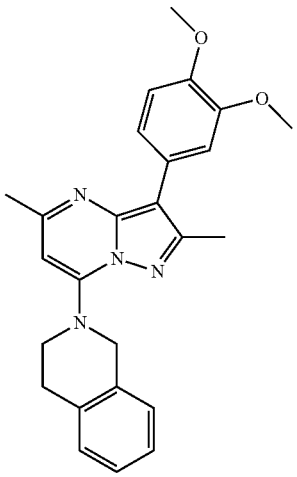 | 2-(3-(3,4-dimethoxyphenyl)-2,5-dimethylpyrazolo[1,5-a]pyrimidin-7-yl)-1,2,3,4-tetrahydroisoquinoline | >50 uM (no observed toxicity or efficacy in either assay tested) |

-continued

| Comp. | Structure | IUPAC Name | IC50 |
|---|---|---|---|
| A0551 | 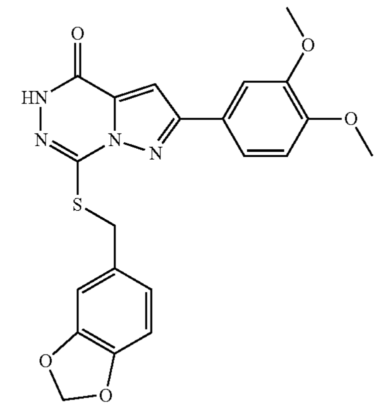 [SMILES: COc1ccc(-c2cc3c(=O)[nH]nc(SCc4ccc5c(c4)OCO5)n3n2)cc1OC] | 7-(benzo[d][1,3]dioxol-5-ylmethylthio)-2-(3,4-dimethoxyphenyl)pyrazolo[1,5-d][1,2,4]triazin-4(5H)-one | >50 uM (no observed toxicity or either assay tested) |
| A0552 | 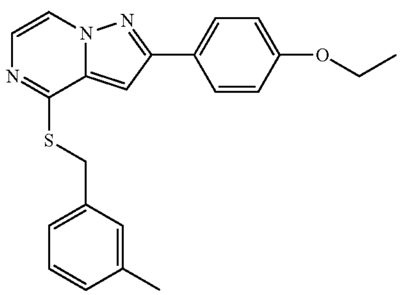 [SMILES: CCOc1ccc(-c2cc3c(SCc4cccc(C)c4)nccn3n2)cc1] | 2-(4-ethoxyphenyl)-4-(3-methylbenzylthio)pyrazolo[1,5-a]pyrazine | >50 uM (no observed toxicity or efficacy in either assay tested) |
| A0553 | 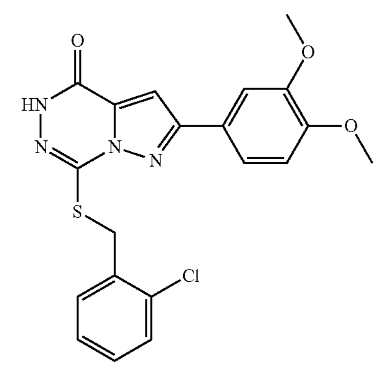 [SMILES: COc1ccc(-c2cc3c(=O)[nH]nc(SCc4ccccc4Cl)n3n2)cc1OC] | 7-(2-chlorobenzylthio)-2-(3,4-dimethoxyphenyl)pyrazolo[1,5-d][1,2,4]triazin-4(5H)-one | >50 uM (no observed toxicity or either assay tested) |

For example, suitable alternative compounds will have a structure according to Formula I

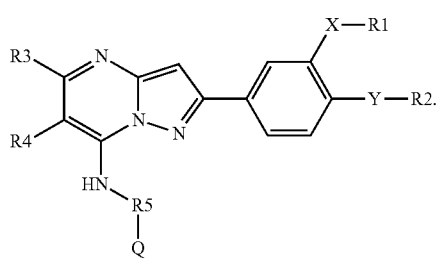

Formula I wherein X and Y are independently O, S, or NR, wherein R, R1, R2, R3, R4, and R5 are independently H, optionally substituted lower alkyl, optionally substituted lower alkenyl, or NR1R2, OH, or halogen; and wherein Q is optionally substituted aryl or optionally substituted heteroaryl. More preferably, X and Y in contemplated compounds are oxygen, and/or R1 and R2 are independently ethyl, methyl, or trifluoromethyl. It is further generally preferred that R3 and R4 are independently lower alkyl, and especially methyl and ethyl, respectively. In still further preferred aspects, R5 is lower alkyl (and especially ethyl), and/or Q is optionally substituted phenyl, or optionally substituted pyridinyl. Particularly preferred compounds include A0435 and A0439 as shown further below.

Figure 6:
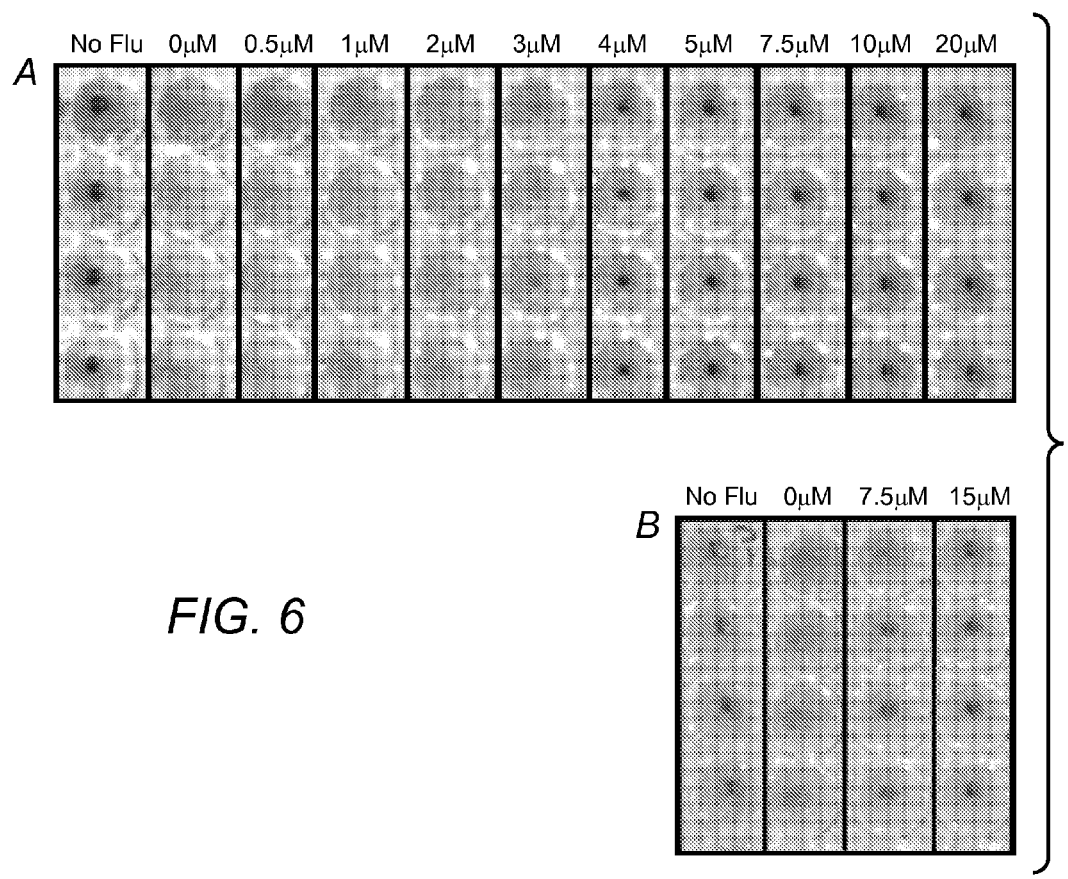
FIG. 6A is a photograph of a hemagglutination assay using an exemplary compound.
FIG. 6B is a photograph illustrating the dose response for the exemplary compound in the same assay.
Figure 7:
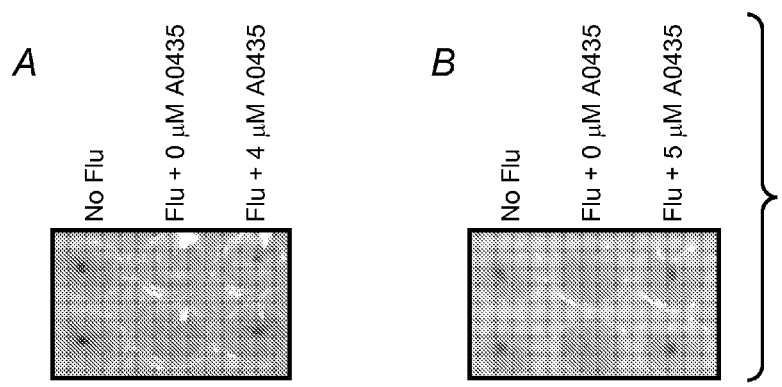
FIGS. 7A and 7B are photographs illustrating inhibition of viral propagation in selected cells using an exemplary compound.
Figure 9:
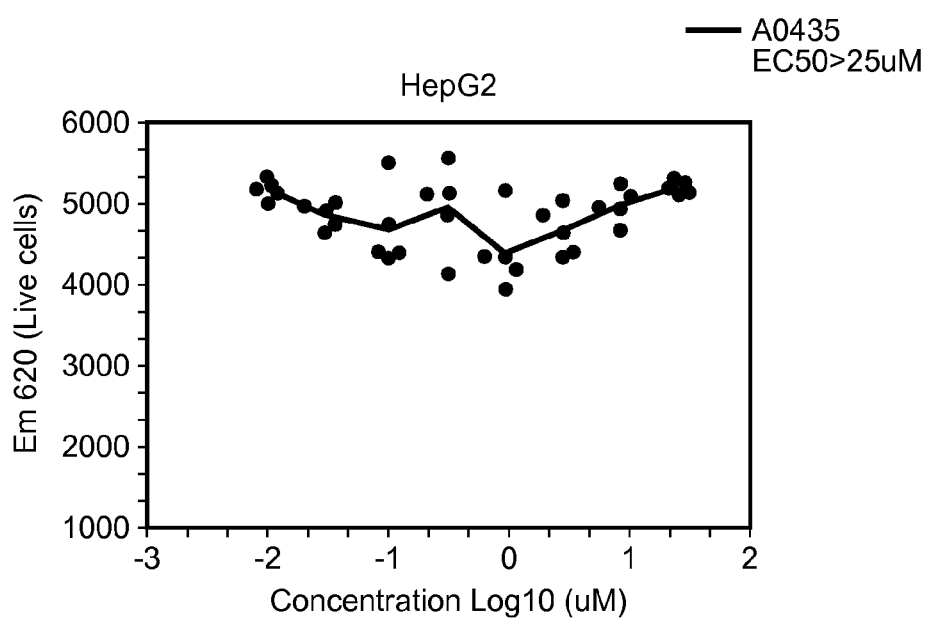
FIGS. 9A and 9B are graphs illustrating cytotoxic activity in selected cells using an exemplary compound.
Figure 9:
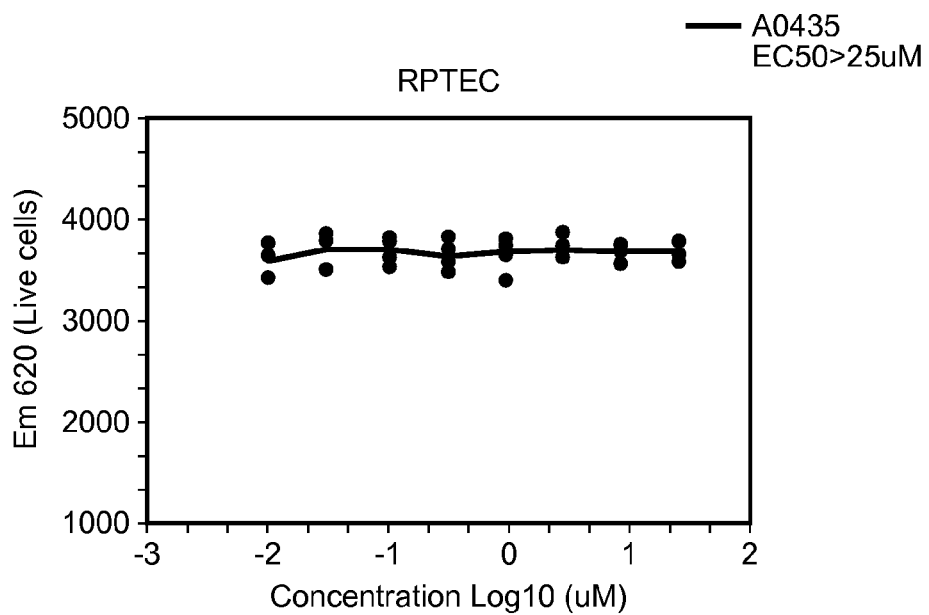

To further evaluate the antiviral potential of A0435 and A0439 in vitro, MDCK cells were pre-incubated with indicated concentrations of compound for 1 hour prior to the addition of live, MDCK-adapted influenza A/Puerto Rico/8/34 (H1N1) virus. After an 18-20 hour incubation, supernatants were collected and evaluated for the presence of viral hemagglutinin activity indicative of successful viral replication using a chicken red blood cell hemagglutination assay. In this type of assay, hemagluttinin activity results in the absence of a characteristic red "button" formed by precipitated red blood cells on the bottom of U-shaped wells. Interestingly, A0435 demonstrated significant antiviral activity at concentrations >4 µM while A0439 demonstrated similar activity at >7.5 µM in accordance with the values observed in the transfection inhibition experiments discussed above as can be seen from FIG. 6 a,b. To determine if the observed antiviral activity of A0435 extended to other viral isolates/serotypes, similar in vitro infection experiments were performed using the influenza A/WS/1933 (H1N1) and the H3N2 serotype A/Aichi/2/68 viruses which were also significantly inhibited by A0435 and the results are shown in FIG. 7 a,b). Of equal importance to drug development, cells infected with live virus demonstrated little to no signs of the cytopathic effects characteristic of influenza A infection as is evident from FIG. 8 a,b,c. Consistent with these results, the inventors found that A0435 is well-tolerated in traditional cellular models of toxicity such as those provided by liver-derived HepG2 cells and primary renal proximal tubule epithelial cells (or RPTEC) over a broad range of concentrations as can be taken from FIG. 9 a,b.

Encouraged by these results, the inventors initiated studies to gauge the antiviral efficacy of A0435 in combating live infection in animals infected with twice the lethal dose 50% (2×LD50) of influenza A/Puerto Rico/8/34. As demonstrated in FIG. 10, ⅗ animals survived infection at day 7 post-infection in the 3.17 mg/kg dosage group, ⅖ animals survived at the 1 mg/kg dose, and 0/5 animals survived when injected with vehicle only (1×PBS, 3% W/V mouse serum albumin).

Consequently, contemplated compounds include all those that can be identified in an inhibition assay as exemplarily shown in FIG. 1. Most preferably, such compounds will have an IC50 of equal or less than 10 µM, even more preferably of equal or less than 1 µM, and most preferably of equal or less than 100 nM, and will have no apparent toxicity at the IC50 as measured above. Thus, a method of identifying contemplated compounds will include a step in which the assay system of FIG. 1 is employed to screen a compound library for inhibitory compounds. Once candidate compounds (typically having IC50 of equal or less than 10 µM) are identified, such compounds can be further modified to ascertain SAR and to produce compounds with higher potency, reduced toxicity, and/or increased bioavailability.

Furthermore it should be noted that the compounds contemplated herein may be prepared as prodrugs. The term "prodrug" as used herein refers to a modification of contemplated compounds, wherein the modified compound exhibits less pharmacological activity (as compared to the modified compound) and wherein the modified compound is converted within a target cell (e.g., B-cell) or target organ/anatomic structure (e.g., joint) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum.

On the other hand, and especially where increased solubility is desired, hydrophilic groups may be added. Still further, where contemplated compounds contain one or more bonds that can be hydrolyzed (or otherwise cleaved), reaction products are also expressly contemplated. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Moreover, especially where contemplated compounds have a higher activity when the compound is metabolized (e.g., hydrolyzed, hydroxylated, glucuronidated, etc.), it should be appreciated that metabolites of contemplated compounds are also expressly contemplated herein.

Additionally, it is contemplated that contemplated compounds may be combined (in vivo or in a pharmaceutical formulation or administration regimen) with at least one other pharmaceutically active ingredient, and especially contemplated other ingredients include various antiviral drugs, various immunomodulatory drugs, and/or anti-inflammatory drugs (e.g., steroids and NSAIDS), etc. Concentrations of second pharmaceutically active ingredients are typically at or preferably below those recommended for stand-alone administration, however, higher concentrations are also deemed suitable for use herein.

Therefore, contemplated pharmaceutical compositions will especially include those in which contemplated compounds (and additional pharmaceutically active ingredients) are provided with a suitable carrier, wherein contemplated compounds are preferably present at a concentration effective to reduce viral propagation in an organism and/or target organ to a degree effective to reduce and more preferably to treat signs and symptoms of a disease associated with the viral infection. Viewed from a different perspective, contemplated compounds are present in a composition in an amount effective to treat a viral infection, and especially a viral infection with an RNA virus (and particularly influenza virus).

For example, virus infections suitable for treatment with contemplated compounds (and especially A0435/A0439) are those produced by infection with an RNA virus (and especially a negative stranded RNA virus), and particularly those viruses bearing the closest resemblance to influenza A. Thus, contemplated viruses include influenza B (which has been confirmed by the inventors as being inhibitable by A0435), and influenza virus C. Phylogenetically related additional viruses suitable for treatment with contemplated compounds include mononegavirales family which includes paramyxoviridae [including Newcastle disease virus; Hendra virus; Nipah virus; rinderpest virus; measles virus; Sendai virus; bovine parainfluenza virus 3; human parainfluenza viruses 1 and 3; mumps virus; parainfluenza viruses 2, 4a, and 4b; metapneumovirus; respiratory syncytial virus], rhabdoviridae [including the mammalian infective vesicular stomatitis virus and rabies virus; the plant infective Strawberry crinkle cytorhabdovirus, lettuce necrotic yellows virus, Cynodon chlorotic streak virus, Maize mosaic virus, Northern cereal mosaic virus, Orchid fleck virus, Rice yellow stunt virus, Sonchus yellows net virus, and Taro vein chlorosis virus; the fish infective Hirame rhabdovirus, infectious hematopoietic necrosis virus, viral hemorrhagic septicemia virus, and Snakehead virus as well as bovine ephemeral fever virus and Adelaide River virus]; the filoviridae [including the hemorrhagic ebolavirus and Marburg viruses] and bornavirus. While the inventors do not have actual data in support of these viruses, it should be noted that an RSV-based expression system can be used to determine suitability of these viruses, and that such system can be prepared by the PHOSITA without undue experimentation.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. In especially preferred aspects, it is contemplated that the formulation is suitable for topical administration, administration via aerosol, and for intrathecal administration. Consequently, especially suitable formulations may be sterile aqueous solutions for topical spray or drop administration, or application as a tincture. Alternatively, suitable topical formulations include creams, ointments, foams, lotions, emulsions, etc. Furthermore, where the compound is formulated for intrathecal administration (e.g., in the treatment of spinal cord injury), it is preferred that the compound is prepared as an injectable solution, suspension, or emulsion. In still further contemplated formulations, contemplated compounds may be formulated for aerosol delivery (e.g., micropowderized, coated onto a dispersible carrier, dissolved in atomizable solvent, etc.)

It should be appreciated that the choice of the particular formulation and carrier will at least in part depend on the specific use and type of compound. There are numerous manners of drug formulation known in the art, and all of those are deemed suitable for use herein (see e.g., Pharmaceutical Preformulation and Formulation: A Practical Guide from Candidate Drug Selection to Commercial Dosage Form by Mark Gibson; Informa HealthCare, ISBN: 1574911201; or Advanced Drug Formulation Design to Optimize Therapeutic Outcomes by Robert O. Williams, David R. Taft, and Jason T. McConville; Informa HealthCare; ISBN: 1420043870).

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

For therapeutic or prophylactic purposes, contemplated compounds are ordinarily combined with one or more excipients appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

Materials and Methods:

Cell-Based Reporter Assays: To identify inhibitors of RdRP, the inventors engineered a mouse cell-based assay system based on the biology of the virus. To create this system, the viral genes encoding PA, PB1, PB2, NP, and NS1 were amplified by reverse transcriptase-polymerase chain reaction (or RT-PCR) of a influenza A/Puerto Rico/8/34 viral cDNA template using gene-specific oligonucleotides. Resulting PCR products were subsequently cloned into a mammalian expression vector (pVAX) utilizing an RNA polymerase II expression cassette and the sequences of the inserts were verified by DNA sequencing. To generate the RNA polymerase I-dependent expression cassette, an RNA polymerase I promoter sequence derived from the 255 bp sequence upstream of the mouse 45S rRNA transcription start site was linked to a multiple cloning site followed by a 33 bp RNA polymerase I termination sequence was generated by PCR using overlapping oligonucleotides and cloned into pBluescript in a similar manner to published reports[12]. This construct, called pPolI, was then digested within the multiple cloning site and directionally ligated to a 5'UTR/luciferase/3'UTR hence generating pPolI-Luc. The pPolI-Luc-DelUTR (i.e. with deleted UTRs) and pPolI-GFP (which possesses UTRs but encodes the green fluorescence protein instead of luciferase) constructs were generated in an analogous fashion.

Transfections were performed using mouse B16-F10 melanoma cells and a commercially available transfection reagent per the manufacturer's suggestions to confirm the system's activity. Briefly, 2 μg of plasmid (e.g. 400 ng of each of constructs encoding PA, PB1, PB2, NP, and pPolI-Luc) were complexed with 15 μL of reagent prior to addition to logarithmically dividing melanoma cells. Transfection complexes were removed after four hours and unless otherwise noted, luciferase activity was assayed 20 hours post-transfection. Experiments involving NS1 were performed in an analogous manner wherein the total amount of plasmid DNA remained fixed at 2 μg but only 333 ng of each plasmid was used due to the need for six plasmids.

Viruses and In Vitro Viral Propagation: Influenza A/Puerto Rico/8/34(H1N1), A/WSN/1933(H1N1), and A/Aichi/2/68 (H3N2) were propagated in canine MDCK cells. On the day preceding infection, MDCK cells were plated in Dulbecco's modified eagle media (D-MEM) supplemented with 10% V/V fetal calf serum and incubated at 37 C at 5% $CO_2$ at densities that would result in 70-90% confluency on the following day. On the day of infection, cells are washed 3 times using complete DMEM/7.5% BSA/25 mM HEPES/(2 ug/mL) TPCK-trypsin prior to receiving virus dilutions.

A0435 Inhibition Studies: For studies involving the B16-F10 transfection system, cells were allowed to recover for 5 hours following the removal of DNA/lipid complexes prior to the addition of indicated amounts of A0435. Luciferase expression was determined 14 hours later. For studies involving inhibition of viral proliferation, cells received indicated amounts of A0435 thirty minutes prior to the addition of virus preparations which were allowed to infect for 2 hours prior to being removed and the recipient cells washed of non-bound virus and the media replaced with corresponding amounts of A0435.

Hemagglutination Assays: Hemagglutination assays were performed as follows. Briefly, 18-20 hours after initial infection, supernatants were incubated with 0.50% chicken red blood cells at a 1:1 ratio (V/V) unless otherwise noted in U-bottom wells and reactions were monitored photographically.

In Vivo Survival Studies: Groups of 5 Balb/C mice (age/gender) were weighed prior to the start of study and injected intravenously at the base of the tail with formulations containing A0435 at doses of 3.17, 1, or 0 mg/kg in phosphate buffered saline containing 3% w/v mouse serum albumin. Four hours later, these mice were challenged intranasally with 2×LD50 of influenza A/Puerto Rico/8/34 under anesthesia. Identical doses of A0435 were administered 24 and 48 hours after the initial dose administration and animal weights were monitored daily. Surviving animals were defined as those who maintained 70% or more of their starting weight.

RELATED ART

1) Fields Virology 5th edition. Edited by David M Knipe and Peter M Howley, Lippincott-Raven, Philadelphia, USA, 2007.
2) Lutz A, Dyall J, Olivo P D, Pekosz A. Virus-inducible reporter genes as a tool for detecting and quantifying influenza A virus replication. J Virol Methods. 2005 June; 126 (1-2):13-20.
3) Hale B G, Randall R E, Ortín J, Jackson D. The multifunctional NS1 protein of influenza A viruses. J Gen Virol. 2008 October; 89(Pt 10):2359-76.
4) Robb N C, Smith M, Vreede F T, Fodor E. NS2/NEP protein regulates transcription and replication of the influenza virus RNA genome. J Gen Virol. 2009 June; 90(Pt 6):1398-407.
5) "Update on oseltamivir resistance to influenza H1N1 (2009) viruses". World Health Organization (WHO). Dec. 15, 2010.
6) Kiso M, Mitamura K; Sakaitagawa Y, Shiraishi K, Kawakami C, Kimura K, Hayden F, Sugaya N, Kawaoka Y. (2004). Resistant influenza A viruses in children treated with oseltamivir: descriptive study. The Lancet 364: 759-765
7) Le M, Kiso M, Someya K, Sakai T, Nguyen H, Nguyen H, Pham D, Ngyen H, Yamada S, Muramoto Y, Horimoto T, Takada A, Goto H, Suzuki T, Suzuki Y, Kawaoka Y. Avian flu: isolation of drug-resistant H5N1 virus. Nature 2005, 437(7062): 1108
8) Dharan N J, Infections with oseltamivir-resistant influenza A(H1N1) virus in the United States. JAMA, 2009. 301(10): p. 1034-41.
9) Gubareva L V, Matrosovich M N, Brenner M K, Bethell R C, Webster R G. Evidence for zanamivir resistance in an immunocompromised child infected with influenza B virus. J Infect Dis. 1998 November; 178(5):1257-62.
10) http://www.cdc.gov/flu/weekly/weeklyarchives2008-2009/weekly35.htm 11) Sheu T G, Fry A M, Garten R J, Deyde V M, Shwe T, Bullion L, Peebles P J, Li Y, Klimov A I, Gubareva L V. Dual resistance to adamantanes and oseltamivir among seasonal influenza A(H1N1) viruses: 2008-2010. J Infect Dis. 2011 Jan. 1; 203(1):13-7.
12) Neumann G, Zobel A, Hobom G. RNA polymerase I-mediated expression of influenza viral RNA molecules. Virology. 1994 July; 202(1):477-9.

Thus, specific embodiments and applications of small molecule inhibitors of influenza A RNA-dependent RNA polymerase have been disclosed. It should be apparent, however, to those skilled in the art that many more modifications besides those already described are possible without departing from the inventive concepts herein. The inventive subject matter, therefore, is not to be restricted except in the spirit of the appended claims.

What is claimed is:

1. A pharmaceutical composition comprising:

a compound according to Formula I in combination with a pharmaceutically acceptable carrier Formula I 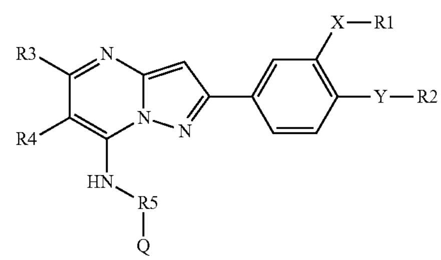 wherein X and Y are independently O, S, or NR;

wherein R, R1, R2, R3, R4, and R5 are independently H, optionally substituted lower alkyl, optionally substituted lower alkenyl, OH, or halogen;

wherein Q is optionally substituted aryl or optionally substituted heteroaryl; and wherein the compound is present in an amount effective to reduce viral propagation of an RNA virus in a patient when the compound is administered to the patient in need thereof.

2. The pharmaceutical composition of claim 1 wherein X and Y are oxygen.

3. The pharmaceutical composition of claim 1 wherein R1 and R2 are independently ethyl, methyl, or trifluoromethyl.

4. The pharmaceutical composition of claim 2 wherein R1 and R2 are independently ethyl, methyl, or trifluoromethyl.

5. The pharmaceutical composition of claim 1 wherein R3 and R4 are independently lower alkyl.

6. The pharmaceutical composition of claim 1 wherein R5 is lower alkyl.

7. The pharmaceutical composition of claim 6 wherein Q is optionally substituted phenyl, or optionally substituted pyridinyl.

8. The pharmaceutical composition of claim 1 wherein the compound is A0435 or A439, or a prodrug thereof.

9. The pharmaceutical composition of claim 1 wherein the RNA virus is an influenza A virus.

10. A method of treating a viral infection in a patient comprising a step of administering the pharmaceutical composition of claim 1 to a patient under a protocol effective to reduce viral propagation of an RNA virus in the patient.

11. The method of claim 10 wherein the compound is A0435 or A439, or a prodrug thereof.

12. The method of claim 10 wherein the RNA virus is an influenza A virus.

* * * * *